United States Patent
Kitada et al.

(10) Patent No.: US 11,602,490 B2
(45) Date of Patent: Mar. 14, 2023

(54) ONE PACK-TYPE DENTAL ADHESIVE COMPOSITION

(71) Applicant: SHOFU INC., Kyoto (JP)

(72) Inventors: Naoya Kitada, Kyoto (JP); Rei Nishimura, Kyoto (JP); Hiroyuki Kobayashi, Kyoto (JP); Kenzo Yamamoto, Kyoto (JP)

(73) Assignee: SHOFU INC., Kyoto (JP)

( * ) Notice: Subject to any disclaimer, the term of this patent is extended or adjusted under 35 U.S.C. 154(b) by 0 days.

(21) Appl. No.: 17/032,335

(22) Filed: Sep. 25, 2020

(65) Prior Publication Data

US 2021/0205181 A1    Jul. 8, 2021

(30) Foreign Application Priority Data

Sep. 26, 2019  (JP) .............................. JP2019-175387

(51) Int. Cl.
  *A61K 6/30*   (2020.01)
  *C08K 5/5419*  (2006.01)
  *C08L 33/10*   (2006.01)
  *C08L 81/08*   (2006.01)

(52) U.S. Cl.
  CPC .............. *A61K 6/30* (2020.01); *C08K 5/5419* (2013.01); *C08L 33/10* (2013.01); *C08L 81/08* (2013.01)

(58) Field of Classification Search
  CPC ....................................................... A61K 6/30
  See application file for complete search history.

(56) References Cited

FOREIGN PATENT DOCUMENTS

| | | | |
|---|---|---|---|
| EP | 1849449 A1 * | 10/2007 | ............. A61K 6/887 |
| JP | 07-277913 | 10/1995 | |
| JP | 2001-072936 | 3/2001 | |
| JP | 2008001624 A * | 1/2008 | |

OTHER PUBLICATIONS

English machine translation of Motoyashiki (JP 2008-0016240) (Year: 2008).*
Extended European Search Report dated Mar. 17, 2021, in corresponding European Patent Application No. 20197848.3.

* cited by examiner

*Primary Examiner* — Michael F Pepitone
(74) *Attorney, Agent, or Firm* — Wenderoth, Lind & Ponack, L.L.P.

(57) ABSTRACT

To provide one liquid type dental adhesive composition that exhibits excellent adhesive property to glass ceramics, oxide-base ceramics and tooth substance, and has excellent storage stability, which are contrary features. One liquid type dental adhesive composition contains (a) silane coupling agent represented by general formula (1), (b) acidic group-containing polymerizable monomer, (c) volatile organic solvent, and (d) water.

[Chemical formula 1]

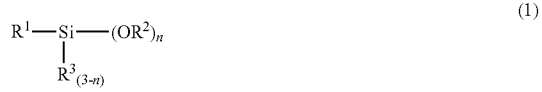

(1)

(In the formula, $R^1$ represents an organic group having at least one functional group selected from the group consisting of a (meth)acryloyl group, a vinyl group and an epoxy group, $R^2$ represents C4-C8 linear alkyl group, $R^3$ represents C1-C8 alkyl group, and n is integer selected from 1 to 3.)

15 Claims, No Drawings

ONE PACK-TYPE DENTAL ADHESIVE COMPOSITION

CROSS-REFERENCE TO RELATED APPLICATIONS

This application is based on and claims the benefit of priory from Japanese Patent Application Serial No. 2019-175387 (filed on Sep. 26, 2019), the contents of which are hereby incorporated by reference in their entirety.

BACKGROUND OF THE INVENTION

Field of the Invention

The present disclosure relates to one liquid type dental adhesive composition that exhibits excellent adhesive property to glass ceramics, oxide-base ceramics and tooth substance, and has excellent storage stability.

Description of the Related Art

In recent years, there has been an increasing demand for aesthetic restoration of patients in dental restoration, and glass ceramics and oxide-based ceramics have become widespread as dental restoration materials. As a dental adhesive composition that exhibits good adhesive strength to these various restoration materials, a dental adhesive composition containing a silane coupling agent and an acidic group-containing polymerizable monomer has been proposed.

However, the dental adhesive composition described in Patent Document 1 is a two-liquid type dental adhesive composition in which a silane coupling agent and an acidic group-containing polymerizable monomer are separately packaged and it is necessary to mix two liquids when using. Therefore, this dental adhesive composition has been a problem that the adhesive operation is complicated.

Also, the dental adhesive composition described in Patent Document 2 is still insufficient in storage stability, and does not exhibit adhesive property to the tooth substance, and therefore another dental adhesive composition is required for using for the tooth substance.

RELEVANT REFERENCES

Patent Literature

[Patent Document 1] Japanese Unexmamined Patent Application Publication No. H7-277913 A
[Patent Document 2] Japanese Unexmamined Patent Application Publication No. 2008-001624 A

SUMMARY OF THE INVENTION

Technical Problem

The present disclosure provides one liquid type dental adhesive composition that exhibits excellent adhesive property to glass ceramics, oxide-base ceramics and tooth substance, and has excellent storage stability, which are contrary features.

Solution to Problem

As a result of intensive studies in view of the above problems, it has been found by the present inventors that the problem is solved by one liquid type dental adhesive composition, containing, (a) silane coupling agent represented by general formula (1), (b) acidic group-containing polymerizable monomer, (c) volatile organic solvent, and (d) water can solve the above problems and the present disclosure have been completed.

[Chemical formula 4]

(1)

(In the formula, $R^1$ represents an organic group having at least one functional group selected from the group consisting of a (meth)acryloyl group, a vinyl group and an epoxy group, $R^2$ represents C4-C8 linear alkyl group, $R^3$ represents C1-C8 alkyl group, and n is integer selected from 1 to 3.)

The (a) silane coupling agent contained in one liquid type dental adhesive composition of the present disclosure preferably satisfies the general formula (2), and more preferably satisfies the general formula (3).

[Chemical formula 5]

$$R^1\text{—Si—}(OR^2)_3 \qquad (2)$$

(In the formula, $R^1$ represents an organic group having at least one (meth)acryloyl group, and $R^2$ represents C4-C8 linear alkyl group.)

[Chemical formula 6]

$$R^1\text{—Si—}(OR^2)_3 \qquad (3)$$

(In the formula, $R^1$ represents a C3-C8 alkyl group having at least one (meth)acryloyl group, and $R^2$ represents C4-C8 linear alkyl group.)

Specifically, it is preferable that a dental primer containing one liquid type dental adhesive composition contains (a) silane coupling agent represented by general formula (1), (b) acidic group-containing polymerizable monomer, (c) volatile organic solvent, and (d) water.

Specifically, it is preferable that the one liquid type dental adhesive composition contains (a) silane coupling agent represented by general formula (1), (b) acidic group-containing polymerizable monomer, (c) volatile organic solvent, and (d) water, and further contains one or more of (e) sulfur atom-containing polymerizable monomer, (f) acidic group-non-containing polymerizable monomer and (g) curing agent.

Advantageous Effects of Invention

The one liquid type dental adhesive composition of the present disclosure exhibits excellent adhesive property to glass ceramics, oxide-base ceramics and tooth substance, and has excellent storage stability.

DETAILED DESCRIPTION OF THE PREFERRED EMBODIMENTS

The one liquid type dental adhesive composition of the present disclosure contains (a) silane coupling agent represented by general formula (1), (b) acidic group-containing polymerizable monomer, (c) volatile organic solvent, and (d) water. The silane coupling agent of the present disclosure is represented by the general formula (1). Specific examples include the following compounds.

[Chemical formula 7]

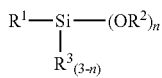

(1)

(In the formula, R¹ represents an organic group having at least one functional group selected from the group consisting of a (meth)acryloyl group, a vinyl group and an epoxy group, R² represents C4-C8 linear alkyl group, R³ represents C1-C8 alkyl group, and n is integer selected from 1 to 3.)

[Chemical Formula 8]

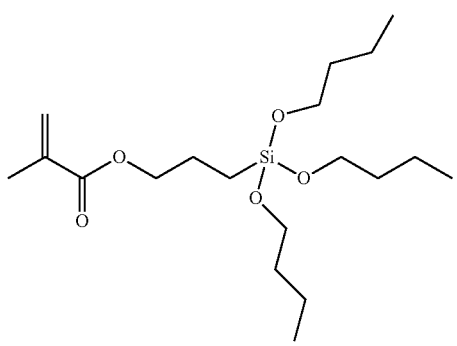

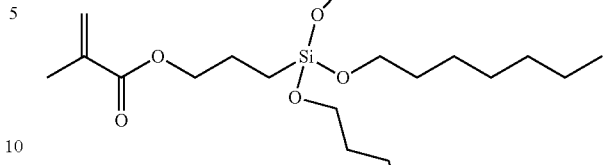

[Chemical 9]

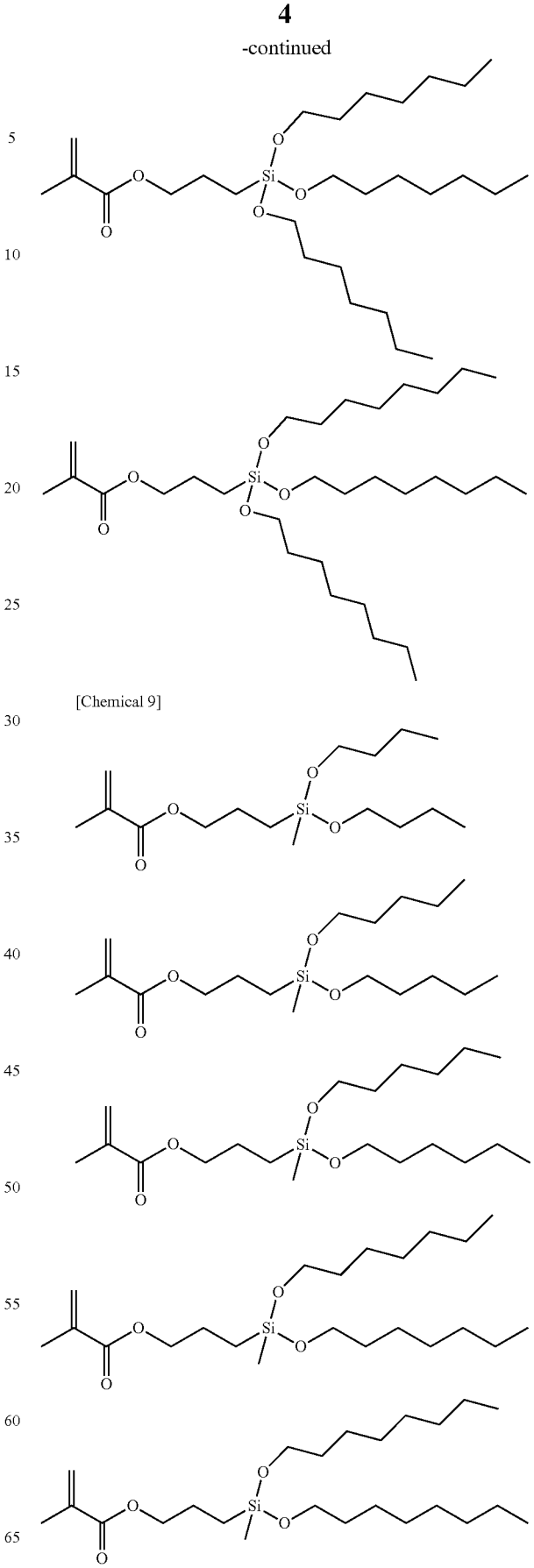

-continued
[Chemical 10]
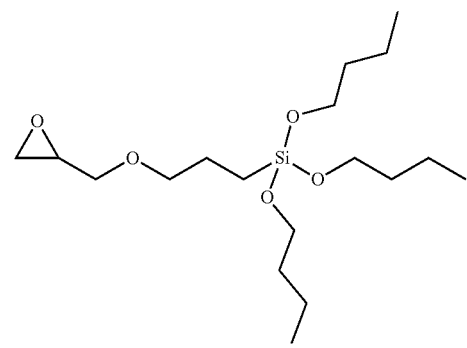
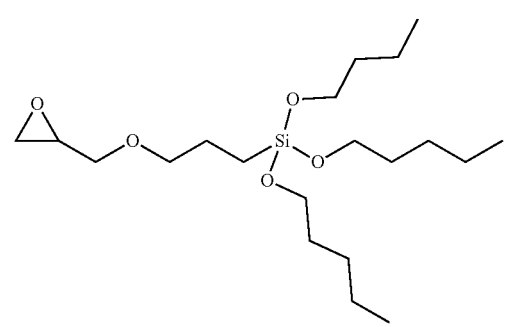
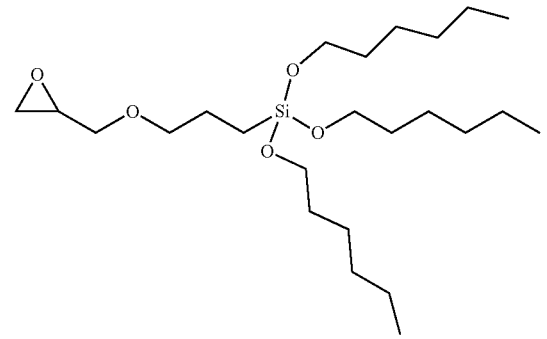
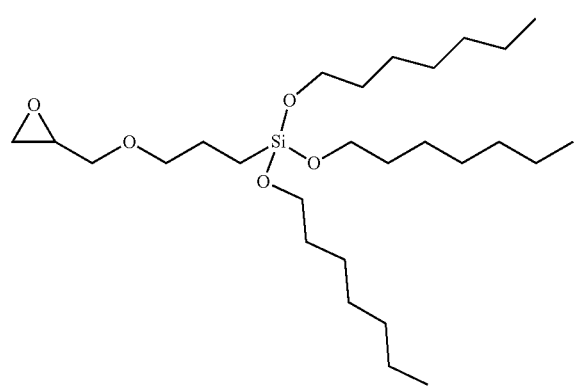
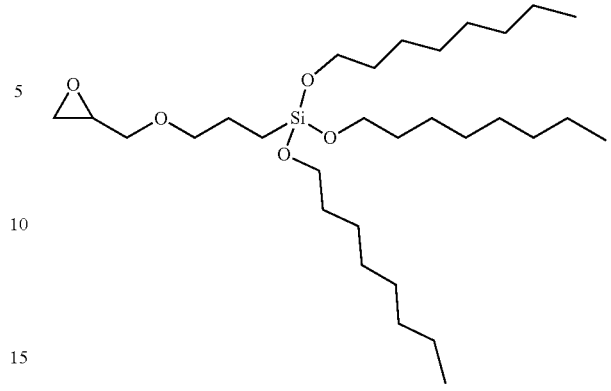
[Chemical formula 11]
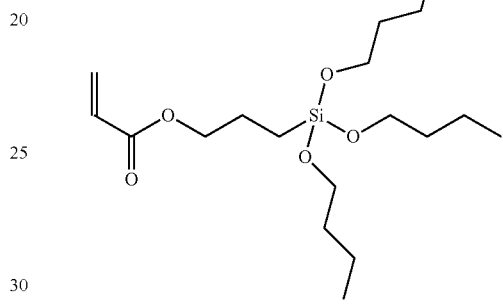
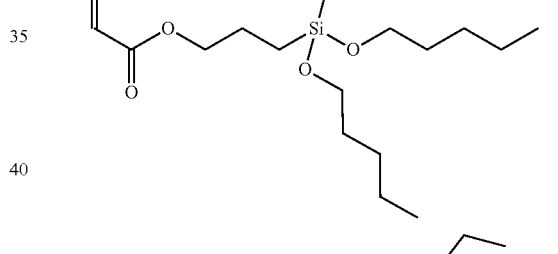
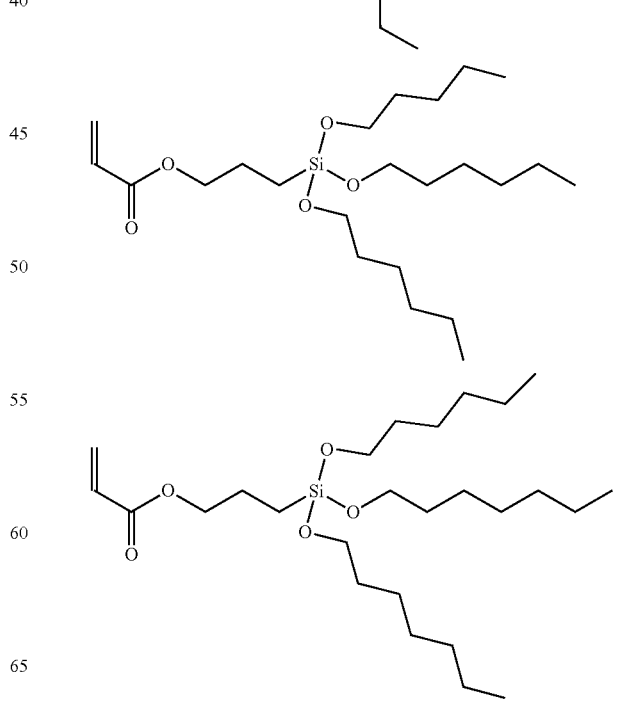

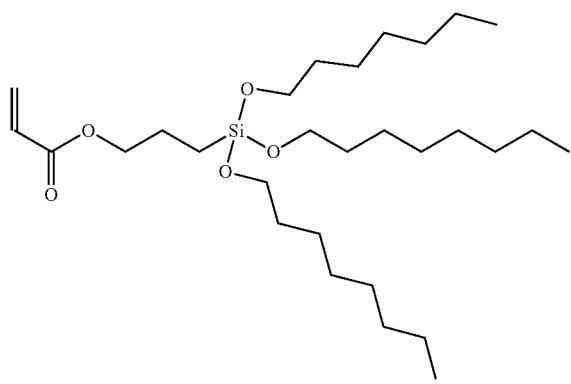
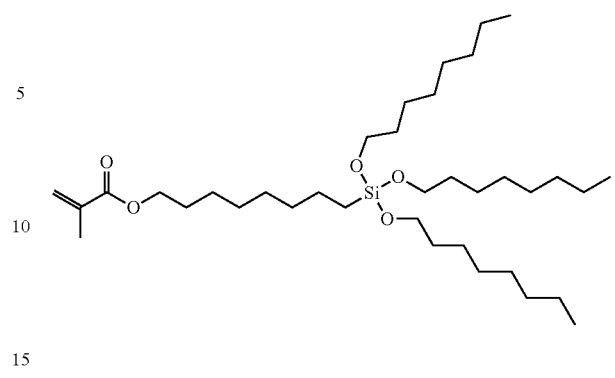
[Chemical formula 12]
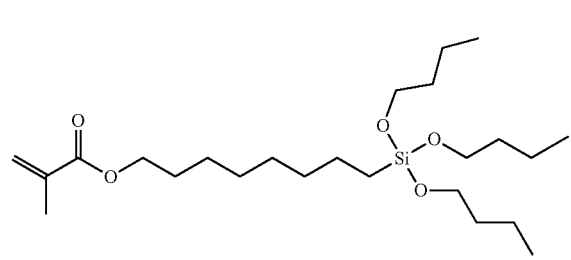
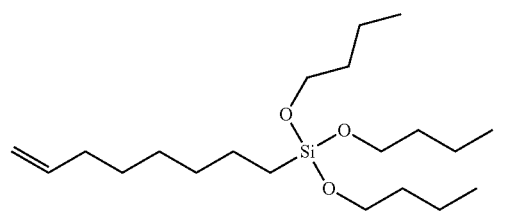
[Chemical formula 13]
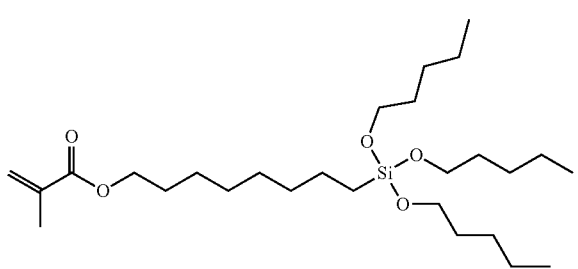
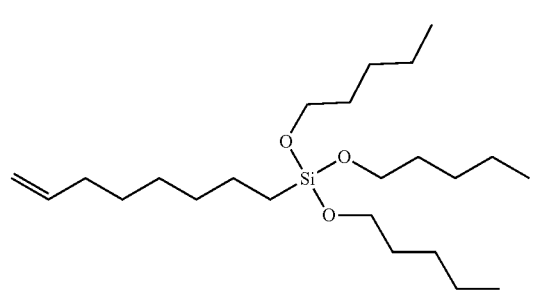
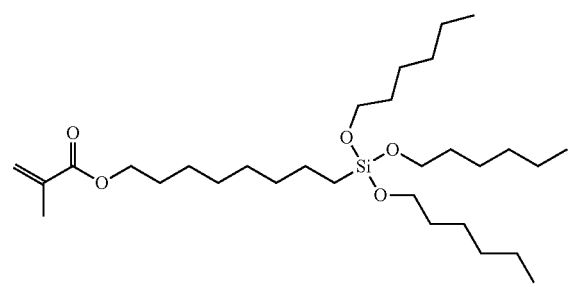
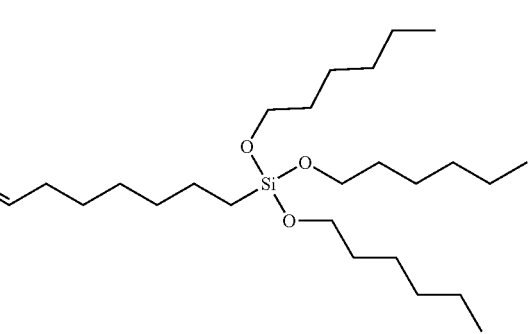
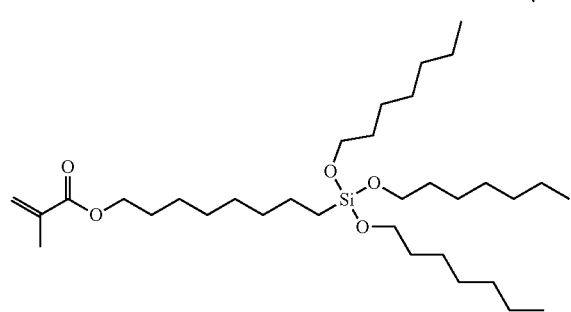
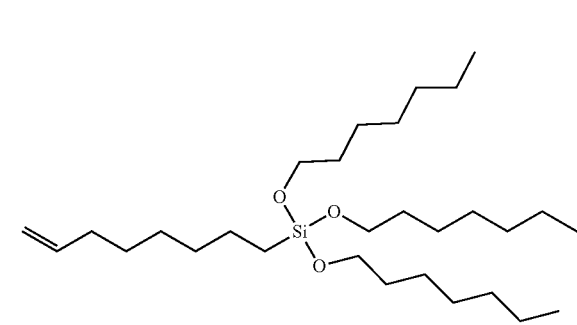

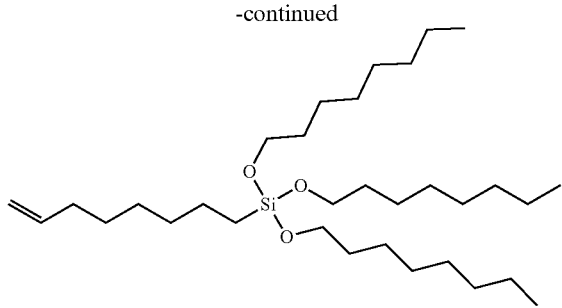

The (a) silane coupling agent can be used singly or in combination of a plurality thereof.

Among the (a) silane coupling agents that satisfy the above general formula (1), from the viewpoint of adhesive property and of excellent compatibility with other components constructing the one liquid type dental adhesive composition such as a volatile organic solvent, it is preferable that the (a) silane coupling agent satisfies the general formula (2) and it is more preferable that the (a) silane coupling agent satisfies the general formula (3). Specific examples of the (a) silane coupling agent satisfying the general formula (3) include the following compounds.

[Chemical formula 14]

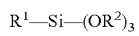
$R^1$—Si—$(OR^2)_3$ (2)

(In the formula, $R^1$ represents an organic group having at least one (meth)acryloyl group, and $R^2$ represents C4-C8 linear alkyl group.)

[Chemical formula 15]

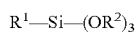
$R^1$—Si—$(OR^2)_3$ (3)

(In the formula, $R^1$ represents a C3-C8 alkyl group having at least one (meth)acryloyl group, and $R^2$ represents C4-C8 linear alkyl group.)

[Chemical formula 16]

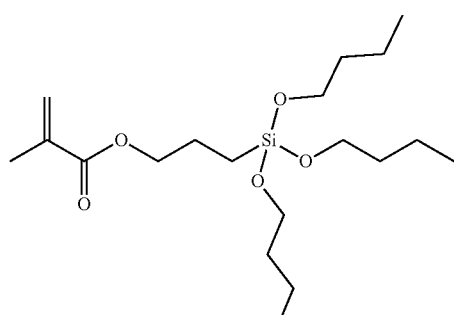

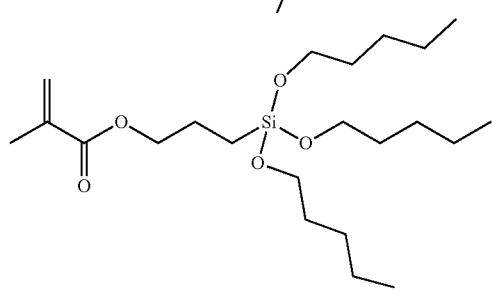

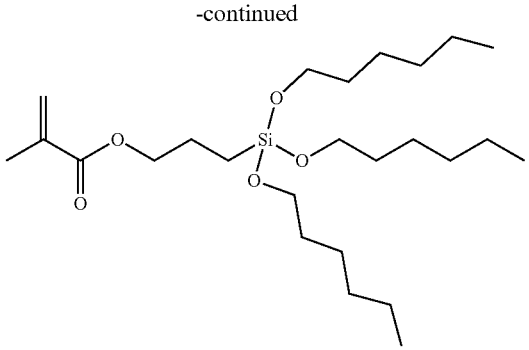

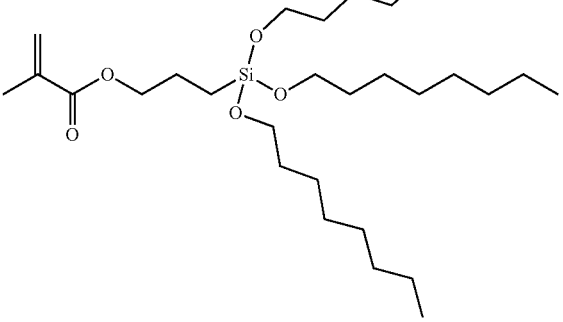

[Chemical formula 17]

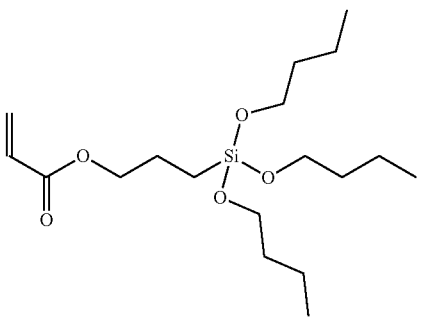

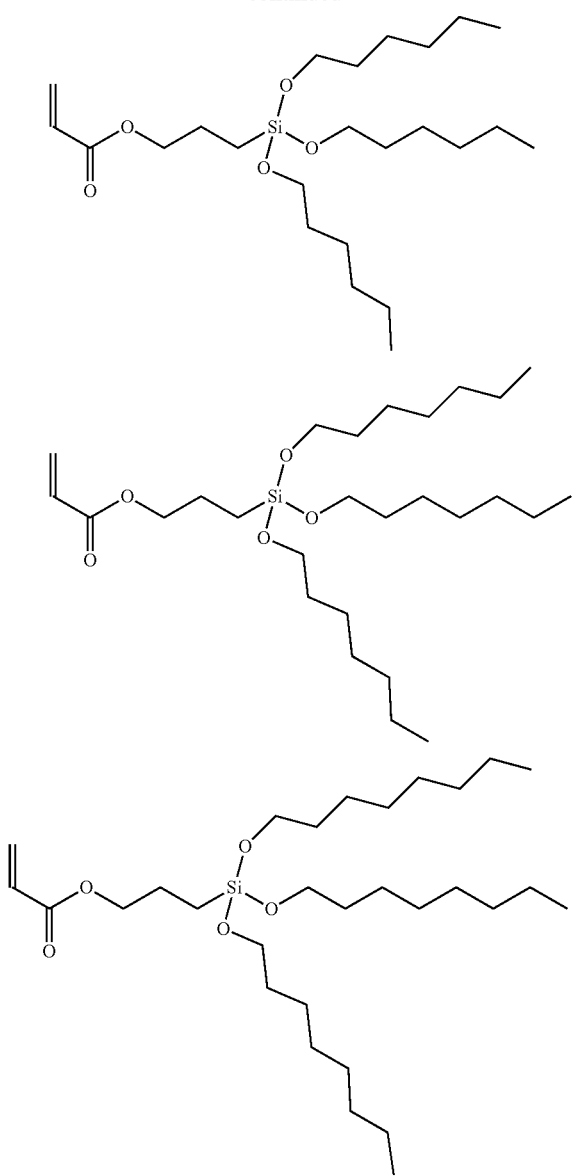
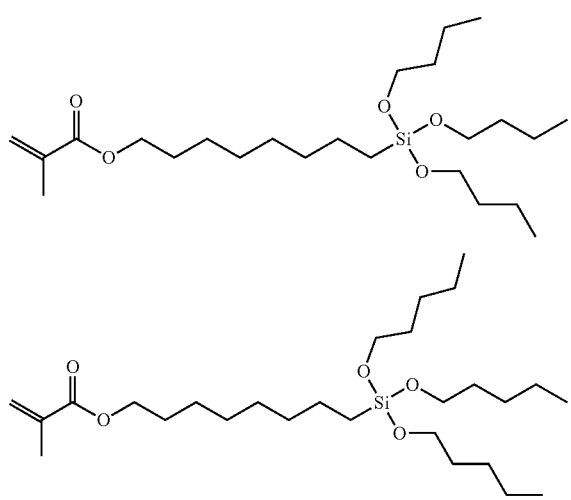

[Chemical formula 18]

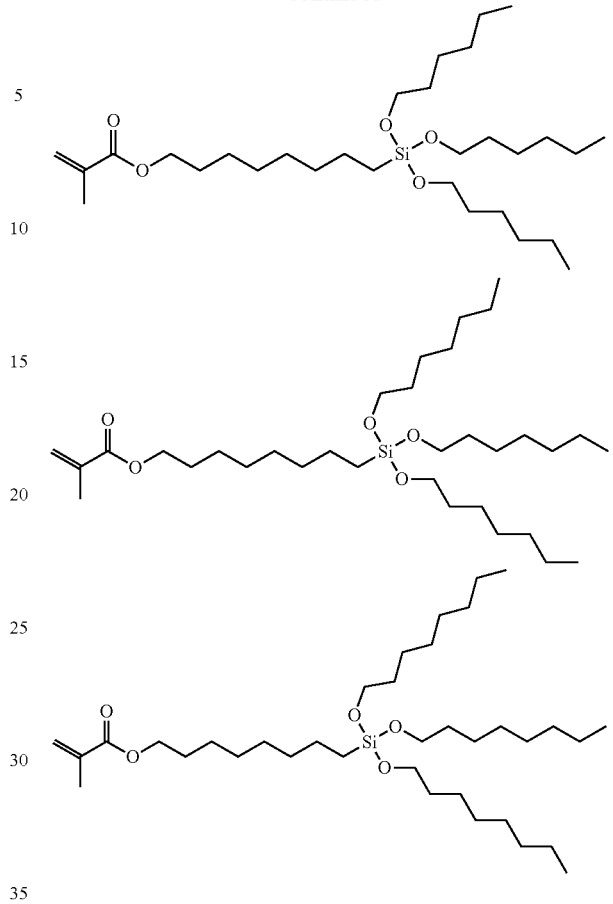

An amount of the (a) silane coupling agent to be compounded in the one liquid type dental adhesive composition of the present disclosure is preferably within a range of 0.01 to 10 parts by weight, more preferably 0.1 to 1 parts by weight based on 100 parts by weight of the total amount of one liquid type dental adhesive composition. When the amount is not within the range of 0.01 to 10 parts by weight, there is a case that adhesive property to glass ceramics decreases. In one liquid type dental adhesive composition of the present disclosure, it is preferable that any silane coupling agent other than the (a) silane coupling agent represented by general formula (1) is not contained, it is preferable that any silane coupling agent other than the (a) silane coupling agent represented by general formula (2) is not contained, and it is preferable that any silane coupling agent other than the (a) silane coupling agent represented by general formula (3) is not contained.

The (b) acidic group-containing polymerizable monomer in the present disclosure may be, for example, a polymerizable monomer having at least one acidic group such as a monovalent phosphate group [phosphinico group: $=P(=O)$ OH], a divalent phosphate group [phosphono group: $-P(=O)(OH)_2$], a pyrophosphate group [$-P(=O)(OH)-O-P(=O)(OH)-$], a carboxylic acid group [a carboxylic group: $-C(=O)OH$, an acid anhydride group: $-C(=O)-O-C(=O)-$] and a sulfonic acid group [sulfone group: $-SO_3H$, $-OSO_3H$], and having at least one polymerizable group (a polymerizable unstaturated group) such as an acryloyl group, a methacryloyl group, a vinyl group, a vinyl benzyl group. Specific examples include followings. In the followings, there is a case that methacryloyl and acryloyl are collectively referred to as (meth)acryloyl.

Specific examples of (b-1) phosphate group-containing polymerizable monomer include 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyicosyl dihydrogen phosphate, bis [2-(meth)acryloyloxyethyl] hydrogens phosphate, bis [4-(meth)acryloyloxybutyl] hydrogen phosphate, bis [6-(meta)acryloyloxyhexyl hydrogen phosphate, bis [8-(meth)acryloyloxyoctyl hydrogen phosphate, bis [9-(meth)acryloyloxynonyl hydrogen phosphate, bis [10-(meth)acryloyloxydecyl hydrogen phosphate, 1,3-di(meth)acryloyloxypropyl dihydrogen phosphate, 2-(meth)acryloyloxyethylphenyl hydrogen phosphate, 2-(meth)acryloyloxyethyl-2-bromoethyl hydrogen phosphate, 2-(meth)acryloyloxy ethylphenylphosphonate, (5-methacryloxypentyl)-3-phosphono propionate, (6-methacryloxyhexyl)-3-phosphono propionate, (10-methacryloxydecyl)-3-phosphono propionate, (6-methacryloxyhexyl)-3-phosphono acetate, (10-methacryloxy decyl)-3-phosphono acetate, 2-methacryloyloxy ethyl-(4-methoxyphenyl)-hydrogen phosphate, 2-methacryloyloxy propyl-(4-methoxyphenyl)-hydrogen phosphate, and acid chlorides, alkali metal salts and amine salts thereof.

Specific examples of (b-2) pyrophosphate group-containing polymerizable monomer include bis [2-(meth)acryloyl oxyethyl] pyrophosphate, bis [(4-(meth)acryloyl oxybutyl] pyrophosphate, bis [6-(meth)acryloyloxy hexyl] pyrophosphate, bis [8-(meth)acryloyloxy octyl] pyrophosphate, bis [10-(meth)acryloyloxy decyl] pyrophosphate, and acid chlorides, alkali metal salts and amine salts thereof.

Specific examples of (b-3) carboxylic acid group-containing polymerizable monomer include maleic acid, methacrylic acid, 4-(meth)acryloyloxy ethoxycarbonyl phthalic acid; 4-(meth)acryloxyethyl trimellitic acid, 4-(meth)acryloyloxybutyl oxycarbonyl phthalic acid, 4-(meth)acryloyloxyhexyl oxycarbonyl phthalic acid, 4-(meth)acryloyloxyoctyl oxycarbonyl phthalic acid, 4-(meth)acryloyloxydecyl oxycarbonyl phthalic acid and acid anhydrides thereof; 5-(meth)acryloyl aminopentyl carboxylic acid, 6-(meth)acryloyloxy-1,1-hexane dicarboxylic acid, 8-(meth)acryloyloxy-1,1-octane dicarboxylic acid, 10-(meth)acryloyloxy-1,1-decane dicarboxylic acid, 11-(meth)acryloyloxy-1,1-undecane dicarboxylic acid, acid chlorides, alkali metal salts and amine salts thereof.

Specific examples of (b-4) sulfonic acid group-containing polymerizable monomer include 2-(meth)acrylamide-2-methylpropane sulfonic acid, styrene sulfonic acid, and 2-sulfoethyl (meth)acrylate, and acid chlorides, alkali metal salts and amine salts thereof.

Among the above described acidic group-containing polymerizable monomers of the (b-1) to (b-4), a polymerizable monomer containing a phosphate group or a pyrophosphate group is preferable, and a polymerizable monomer containing a divalent phosphate group [phosphono group: —P(=O)(OH)$_2$] is more preferable. Among them, a polymerizable monomer containing a divalent phosphate group which has, in the molecule, an alkyl group or an alkylene group that the number of carbon in the main chain is 6 to 20 is more preferable, and a polymerizable monomer containing a divalent phosphate group which has, in the molecule, an alkylene group that the number of carbon in the main chain is 8 to 12 such as 10-methacryloyloxydecyl dihydrogenphosphate is more preferable.

The (b) acidic group-containing polymerizable monomer can be used singly or in combination of a plurality thereof. An amount of the (b) acidic group-containing polymerizable monomer to be compounded is preferably 0.1 to 50 parts by weight, more preferably 5 to 20 parts by weight based on 100 parts by weight of the total amount of one liquid type dental adhesive composition. When the amount is not within the range of 0.1 to 50 parts by weight, there is a case that adhesive property to tooth substance and oxide ceramics decreases.

As for the (c) volatile organic solvent in this disclosure, an organic solvent typically having a boiling point of 150° C. or lower under ordinary pressure and having a solubility, in water at 25° C., of 5 weight % or more, more preferably 30 weight % or more, most preferably soluble in water in any desired proportion can be used. Among them, a water soluble volatile organic solvent having a boiling point of 100° C. or lower under ordinary pressure is preferable and specific examples thereof include ethanol, methanol, 1-propanol, isopropyl alcohol, acetone, methyl ethyl ketone, 1,2-dimethoxyethane, 1,2-diethoxyethane and tetrahydrofuran. Among the above described water soluble volatile organic solvents, acetone, methyl ethyl ketone, 1,2-dimethoxyethane, 1,2-diethoxyethane and tetrahydrofuran are more preferable.

The (c) volatile organic solvent can be used singly or in combination of a plurality thereof. An amount of the (c) volatile organic solvent to be compounded is preferably within a range of 10 to 90 parts by weight, more preferably 30 to 60 parts by weight based on 100 parts by weight of the total amount of one liquid type dental adhesive composition. When the amount is not within the range of 10 to 90 parts by weight, there is a case that solubility and adhesive property decrease. It is preferable that the one liquid type dental adhesive composition of the present disclosure does not contain organic solvent other than the (c) volatile organic solvent.

Specific examples of the (d) water compounded in the present disclosure include deionized water and distilled water. In addition, an amount of the (d) water to be compounded is preferably within a range of 9 to 50 parts by weight, and is more preferably within a range of 25 to 35 parts by weight based on 100 parts by weight of the total amount of one liquid type dental adhesive composition. When the amount is not within the range of 9 to 50 parts by weight, there is a case that adhesive property to tooth substance decrease.

In order to exhibit adhesive property to precious metal alloy, the (e) sulfur atom-containing polymerizable monomer may be compounded in the one liquid type dental adhesive composition of the present disclosure. Any known compounds can be used as the (e) sulfur atom-containing polymerizable monomer of the present disclosure without any limitation, as long as it contains at least one sulfur atom (excluding sulfur atom that constitutes an acidic group containing sulfur atom such as sulfo group) and one or more polymerizable unsaturated groups in the molecule. As the polymerizable unsaturated group, an acryloyl group, a methacryloyl group, an acrylamide group and a methacrylamide group and the like are preferable from the viewpoint of adhesive property. Further, the sulfur atom is contained in a form that the sulfur atom does not form an acidic group such as a sulfone group in the molecule, and is contained in a form that the sulfur atom forms a partial structure other than an acidic group by forming a partial structure such as >C=S, >C—S—C< in the molecule. It is preferable that the (e) sulfur atom-containing polymerizable monomer does not contain an acidic group. Examples of the (e) sulfur atom-containing polymerizable monomer include a compound capable of generating a mercapto group by tautomerism, a disulfide compound, a chain or cyclic thioether compound and the like. Specific examples include 10-methacryloxy decyl-6,8-dithiooctanate, 6-methacryloxy hexyl-6,8-dithiooctanate, 6-methacryloyloxy hexyl-2-thiouracil-5-carboxylate, 2-(11-methacryloyloxy undecylthio)-5-mercapto-1,3,4-thiadiazole.

The (e) sulfur atom-containing polymerizable monomer can be used singly or in combination of a plurality thereof. An amount of the (e) sulfur atom-containing polymerizable monomer to be compounded is preferably within a range of 0.01 to 10 parts by weight based on 100 parts by weight of the total amount of one liquid type dental adhesive composition. When the amount is not within the range of 0.01 to 10 parts by weight, there is a case that adhesive property to precious metal alloy decrease.

In order to improve adhesive property to tooth substance, the (f) acidic group-non-containing polymerizable monomer may be compounded in the one liquid type dental adhesive composition of the present disclosure. The (f) acidic group-non-containing polymerizable monomer is a polymerizable monomer having at least one polymerizable unsaturated group and having no acidic group in the molecule. Any known compounds can be used as the (f) acidic group-non-containing polymerizable monomer without any limitation, as long as it is a polymerizable monomer other than the (a) silane coupling agent and the (e) sulfur atom-containing polymerizable monomer. As the polymerizable unsaturated group of such polymerizable monomer, an acryloyl group, a methacryloyl group, an acrylamide group and a methacrylamide group and the like are preferable from the viewpoint of adhesive property.

Specific Examples of the (f) acidic group-non-containing polymerizable monomer that can be suitably used in the present disclosure include monofunctional polymerizable monomer such as methyl (meth)acrylate, ethyl (meth)acrylate, butyl (meth)acrylate, glycidyl (meth)acrylate, 2-cyanomethyl (meth)acrylate, benzyl methacrylate, polyethylene glycol mono (meth)acrylate, allyl (meth)acrylate, 2-hydroxyethyl (meth)acrylate, 3-hydroxypropyl (meth)acrylate and glyceryl mono (meth)acrylate; polyfunctional polymerizable monomer such as ethylene glycol di(meth)acrylate, diethylene glycol di(meth)acrylate, triethylene glycol di(meth)acrylate, nonaethylene glycol di(meth)acrylate, propylene glycol di(meth)acrylate, dipropylene glycol di(meth)acrylate, 2,2'-bis [4-(meth)acryloyloxy ethoxyphenyl] propane, 2,2'-bis [4-(meth)acryloyloxy ethoxyethoxyphenyl] propane, 2,2'-bis [4-(meth)acryloyloxy ethoxyethoxyethoxyphenyl] propane, 2,2'-bis {4-[2-hydroxy-3-(meth)acryloyloxy propoxy] phenyl} propane, 1,4-butanediol di(meth)acrylate, 1,6-hexanediol di(meth)acrylate, 1,9-nonandiol di(meth)acrylate, trimethylprop an tri(meth)acrylate, neopentylglycol di(meth)acrylate, 1,6-bis (methacrylethyl oxycarbonylamino)-2,2,4-trimethylhexane, 1,6-bis (methacrylethyl oxycarbonylamino)-2,4,4-trimethylhexane, urethane (meth)acrylate, epoxy (meth)acrylate, trimethylpropan trimethacrylate, pentaerythritol tetramethacrylate and the like; fumarate compounds such as monomethyl fumarate, diethyl fumarate, diphenyl fumarate; styrene such as styrene, divinylbenzene, α-methylstyrene, α-methylstyrene dimer, and α-methylstyrene derivative; and allyl compounds such as diallyl phthalate, diallyl terephthalate, diallyl carbonate and allyl diglycol carbonate.

Among the above described (f) acidic group-non-containing polymerizable monomer, a polyfunctional polymerizable monomer is preferably used particularly. Specific examples of the preferably used polyfunctional polymerizable monomer include 2,2'-bis {4-[2-hydroxy-3-(meth)acryloyl oxypropoxy] phenyl} propane, triethylene glycol methacrylate, 2,2-bis [(4-(meth)acryloyloxy polyethoxyphenyl) propane], 1,6-bis (methacrylethyl oxycarbonylamino)-2,2,4-trimethylhexane, 1,6-bis (methacrylethyl oxycarbonylamino)-2,4,4-trimethylhexane, and trimethylpropane trimethacrylate.

The above described (f) acidic group-non-containing polymerizable monomer may be used singly or as a mixture of two or more. An amount of the (f) acidic group-non-containing polymerizable monomer to be compounded in the one liquid type dental adhesive composition is preferably 5 to 50 parts by weight based on 100 parts by weight of the total amount of one liquid type dental adhesive composition. When the amount exceeds 50 parts by weight, there is a case that adhesive property decreases.

The (g) curing agent may be compounded in the one liquid type dental adhesive composition of the present disclosure. As the (g) curing agent in the present disclosure, known curing agents can be used. Specific examples include polymerization initiators such as (g-1) α-diketones, (g-2) ketals, (g-3) thioxanthones, (g-4) acylphosphine oxides, (g-5) coumarins, (g-6) halomethyl group substitution-s-triazine derivatives and (g-7) peroxides, and polymerization accelerators such as (g-8) aromatic tertiary amines, (g-9) aliphatic tertiary amines, (g-10) sulfinic acids and salts thereof, (g-11) aldehydes and (g-12) compounds having a thiol group. Among them, the (g-1) α-diketones and the (g-4) acylphosphine oxides which are photopolymerization type polymerization initiators (photopolymerization initiators) are preferable because excellent curability is imparted to the one liquid type dental adhesive composition of the present disclosure.

Examples of the (g-1) α-diketones include camphorquinone, benzyl and 2,3-pentanedione.

Examples of the (g-2) ketals include benzyl dimethyl ketal and benzyl diethyl ketal.

Examples of the (g-3) thioxanthones include 2-chlorothioxanthone and 2,4-diethylthioxanthone.

Examples of the (g-4) acylphosphine oxides include 2,4, 6-trimethylbenzoyl diphenylphosphine oxide, his (2,4,6-trimethylbenzoyl) phenylphosphine oxide, dibenzoylphenylphosphine oxide, his (2,6-dimethoxybenzoyl) phenylphosphine oxide, tris (2,4-dimethylbenzoyl) phosphine oxide, tris (2-methoxybenzoyl) phosphine oxide, 2,6-dimethoxybenzoyl diphenylphosphine oxide, 2,6-dichlorobenzoyl diphenylphosphine oxide, 2,3,5,6-tetramethylbenzoyl diphenylphosphine oxide, benzoyl-bis (2,6-dimethylphenyl)phosphonate and 2,4,6-trimethylbenzoyl ethoxyphenylphosphine oxide.

Examples of the (g-5) coumarins include 3,3'-carbonyl his (7-diethylamino) coumarin, 3-(4-methoxybenzoyl) coumarin and 3-chenoyl coumarin.

Examples of the (g-6) halomethyl group substitution-s-triazine derivatives include 2,4,6-tris(trichloromethyl)-s-triazine, 2,4,6-tris(tribromomethyl)-s-triazine and 2-methyl-4, 6-bis(trichloromethyl)-s-triazine.

Examples of the (g-7) peroxides include diacyl peroxides, peroxyesters, dialkyl peroxides, peroxyketals, ketone peroxides, and hydroperoxides. Specific examples of diacyl peroxides include benzoyl peroxide, 2,4-dichlorobenzoyl peroxide and m-toluoyl peroxide. Specific examples of peroxyesters include t-butylperoxy benzoate, bis-t-butylperoxy isophthalate, 2,5-dimethyl-2,5-bis (benzoylperoxy) hexane, t-butylperoxy-2-ethylhexanoate and t-butylperoxy isopropyl carbonate. Specific examples of dialkyl peroxides include dicumyl peroxide, di-t-butyl peroxide and lauroyl peroxide. Specific examples of peroxyketals include 1,1-bis (t-butylperoxy)-3,3,5-trimethyl cyclohexane. Specific examples of ketone peroxides include methylethylketone peroxide, cyclohexanone peroxide, methyl acetoacetate peroxide. Specific examples of hydroperoxides include t-butylhydro peroxide, cumenehydro peroxide and p-diisopropylbenzene peroxide.

Examples of the (g-8) aromatic tertiary amines include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis (2-hydroxyethyl)-3,5-dimethylaniline, N,N-bis (2-hydroxyethyl)-p-toluidine, N,N-bis (2-hydroxyethyl)-3,4-dimethylaniline, N,N-bis (2-hydroxyethyl)-4-ethylaniline, N,N-bis (2-hydroxyethyl)-4-isopropylaniline, N,N-bis (2-hydroxyethyl)-4-t-butylaniline, N,N-bis (2-hydroxyethyl)-3,5-di-isopropylaniline, N,N-bis(2-hydroxyethyl)-3,5-di-t-butylaniline, 4-N,N-dimethylamino benzoicacid ethylester, 4-N,N-dimethylamino benzoicacid methylester, 4-N,N-dimethylamino benzoicacid-n-butoxyethylester, 4-N,N-dimethylaminobenzoicacid-2-(methacryloyloxy)ethylester, 4-N,N-dimethylamino benzophenone.

Examples of the (g-9) aliphatic tertiary amines include trimethylamine, triethylamine, N-methyl diethanolamine, N-ethyl diethanolamine, N-n-butyl diethanolamine, N-lauryl diethanolamine, triethanolamine, 2-(dimethylamino) ethylmethacrylate, N-methyl diethanolamine dimethacrylate, N-ethyl diethanolamine dimethacrylate, triethanolamine monomethacrylate, triethanolamine dimethacrylate, triethanolamine trimethacrylate.

Examples of the (g-10) sulfinic acids and salts thereof include benzenesulfinic acid, sodium benzenesulfinate, potassium benzenesulfinate, calcium benzenesulfinate, lithium benzenesulfinate, toluene sulfinic acid, sodium toluenesulfinate, potassium toluenesulfinate, calcium toluenesulfinate, lithium toluenesulfinate, 2,4,6-trimethylbenzene sulfinate, sodium 2,4,6-trimethylbenzene sulfinate, potassium 2,4,6-trimethylbenzene sulfinate, calcium 2,4,6-trimethylbenzene sulfinate, lithium 2,4,6-trimethylbenzene sulfinate, 2,4,6-triethylbenzene sulfinate, sodium 2,4,6-triethylbenzene sulfinate, potassium 2,4,6-triethylbenzene sulfinate, calcium 2,4,6-triethylbenzene sulfinate, 2,4,6-isopropylbenzene sulfinate, sodium 2,4,6-triisopropylbenzene sulfinate, potassium 2,4,6-triisopropylbenzene sulfinate, and calcium 2,4,6-triisopropylbenzene sulfinate.

Examples of the (g-11) aldehydes include dimethylamino benzaldehyde, and terephthal aldehyde.

Examples of the (g-12) compounds having a thiol group include 2-mercapto benzoxazole, decanethiol, 3-mercaptopropyl trimethoxysilane, and thiobenzoic acid.

The (g) curing agent can be used singly or in combination of a plurality thereof. An amount of the (g) curing agent to be compounded is preferably within a range of 0.01 to 10 parts by weight based on 100 parts by weight of the total amount of one liquid type dental adhesive composition from the view point of adhesive property.

The (h) filler may be compounded in the one liquid type dental adhesive composition of the present disclosure. By compounding the filler, it is possible to improve the mechanical strength of the adhesive material layer. Examples of the filler include (h-1) inorganic filler, (h-2) organic filler (h-2), and (h-3) composite filler of an inorganic filler and an organic filler.

Examples of the (h-1) inorganic filler include silica; silica-based minerals such as kaolin, clay, mica, and mica; ceramics and glasses that are based on silica and contain $Al_2O_3$, $B_2O_3$, $TiO_2$, $ZrO_2$, $BaO$, $La_2O_3$, $SrO_2$, $CaO$, $P_2O_5$, and the like. As the glasses, lanthanum glass, barium glass, strontium glass, soda glass, lithium borosilicate glass, zinc glass, fluoroaluminosilicate glass, borosilicate glass and bioglass are preferably used. Crystalline quartz, hydroxyapatite, alumina, titanium oxide, yttrium oxide, zirconia, calcium phosphate, barium sulfate, aluminum hydroxide, sodium fluoride, potassium fluoride, sodium monofluoro phosphate, lithium fluoride and ytterbium fluoride are also preferably used.

Examples of the (h-2) organic filler include polymethyl methacrylate, polyethyl methacrylate, a polymer of polyfunctional methacrylate, polyamide, polystyrene, polyvinyl chloride, chloroprene rubber, nitrile rubber and styrene-butadiene rubber.

Examples of the (h-3) composite filler of an inorganic filler and an organic filler include an inorganic/organic composite filler in which an inorganic filler is dispersed in an organic filler or an inorganic filler is coated with various polymerizable monomers.

In order to improve curability, mechanical strength and application property, the filler (h) may be surface-treated with a known surface treatment agent such as a silane coupling agent before use. Examples of the surface treatment agent include vinyltrimethoxysilane, vinyltriethoxysilane, vinyltrichlorosilane, vinyltri (β-methoxyethoxy)silane, γ-methacryloyloxypropyl trimethoxysilane, γ-glycidoxypropyl trimethoxysilane, γ-mercaptopropyl trimethoxysilane and γ-aminopropyl triethoxysilane.

As the filler (h), a fine particle filler having a primary particle diameter of 0.001 to 0.1 µm is preferably used from the viewpoint of adhesive strength, application property and the like. Specific examples include "Aerosil OX50", "Aerosil 50", "Aerosil 200", "Aerosil 380", "Aerosil R972", and "Aerosil 130" (all of which are manufactured by Nippon Aerosil Co., Ltd., and trade names).

The (h) filler can be used singly or in combination of a plurality thereof. An amount of the (h) filler to be compounded is preferably within a range of 0.1 to 30 parts by weight based on 100 parts by weight of the total amount of one liquid type dental adhesive composition from the view point of adhesive property.

The one liquid type dental adhesive composition of the present disclosure may contain a stabilizer (polymerization inhibitor), a colorant, a fluorescent agent and an ultraviolet absorber. In addition, antibacterial substances such as cetylpyridinium chloride, benzalkonium chloride, (meth) acryloyloxy dodecylpyridinium bromide, (meth)acryloyloxy hexadecylpyridinium chloride, (meth)acryloyloxy decylammonium chloride, triclosan and the like may be also contained.

EXAMPLES

The present disclosure is described in more detail with reference to Examples. However, the present disclosure is not limited to Examples. Materials used in Examples and Comparative Examples are as follows.

[(a) Silane Coupling Agent]

[Chemical formula 19]

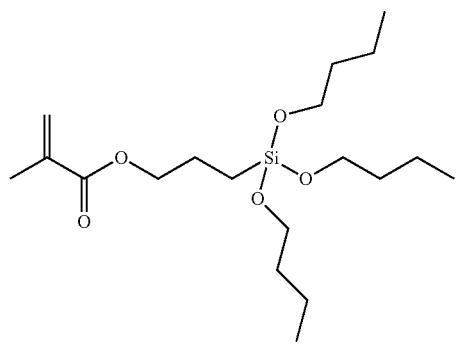

SC1

3-(tributoxysilyl)propyl methacrylate

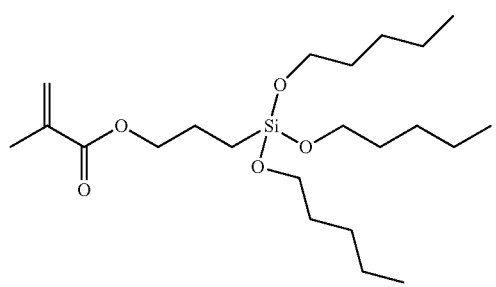

SC2

3-(tris(pentyloxy)silyl)propyl methacrylate

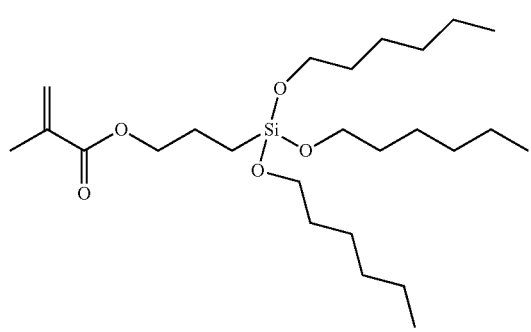

SC3

3-(tris(hexyloxy)silyl)propyl methacrylate

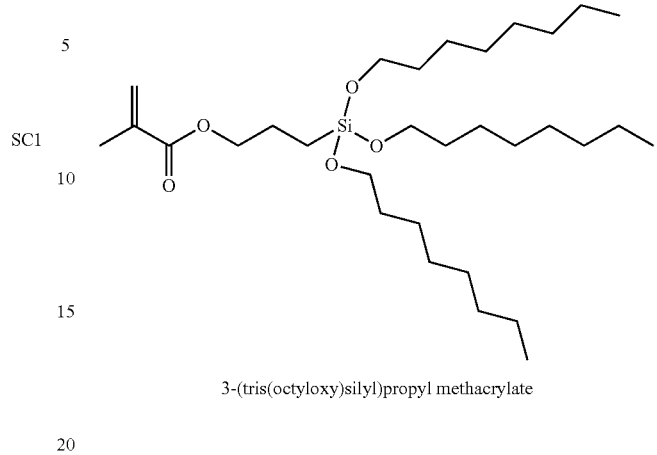

SC4

3-(tris(octyloxy)silyl)propyl methacrylate

[Silane Coupling Agent not Satisfying the General Formula (1)]

[Chemical formula 20]

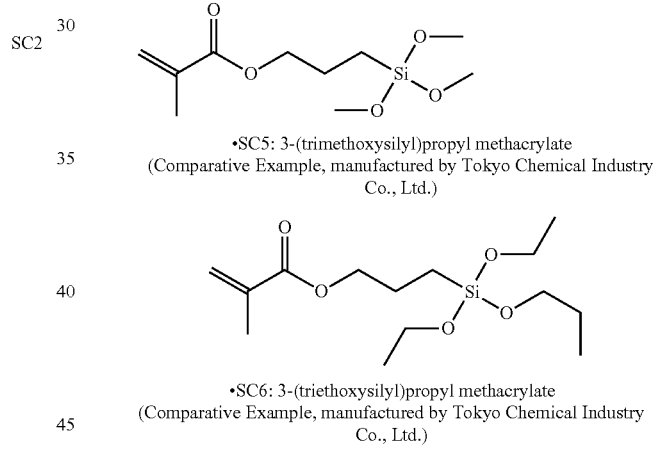

• SC5: 3-(trimethoxysilyl)propyl methacrylate
(Comparative Example, manufactured by Tokyo Chemical Industry Co., Ltd.)

• SC6: 3-(triethoxysilyl)propyl methacrylate
(Comparative Example, manufactured by Tokyo Chemical Industry Co., Ltd.)

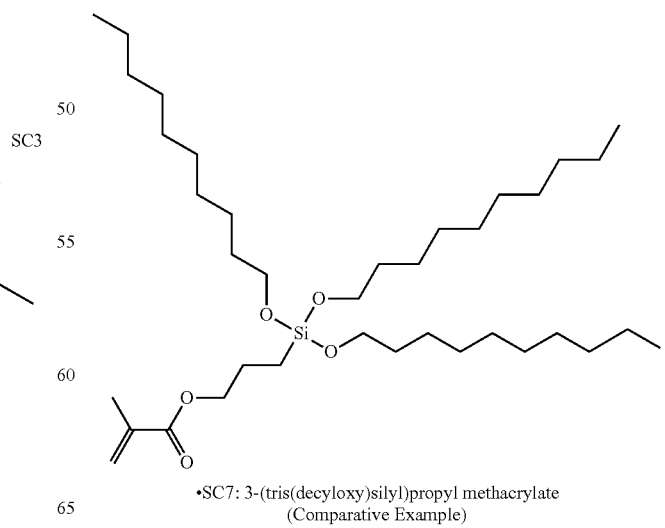

• SC7: 3-(tris(decyloxy)silyl)propyl methacrylate
(Comparative Example)

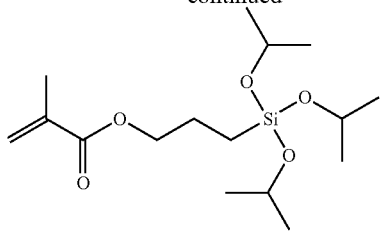

•SC8: 3-(triisopropoxysilyl)propyl methacrylate
(Comparative Example, manufactured by Gelest, Inc.)

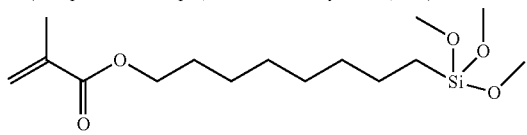

•SC9: 8-(trimethoxysilyl)octyl methacrylate
(Comparative Example, manufactured by Shin-Etsu Chemical Co., Ltd.)

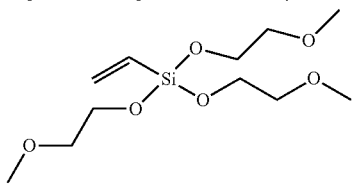

SC10: Vinyltris(2-methoxyethoxy)silane)
(Comparative Example, manufactured by Tokyo Chemical Industry Co., Ltd.)

[(b) Acidic Group-Containing Polymerizable Monomer]
6-MHPA: 6-methacryloxyhexyl-phosphonoacetate
4-MET: 4-methacryloxyethyl trimelliate
10-MDP: 10-methacryloyloxydecyl dihydrogen phosphate
[(c) Volatile Organic Solvent]
Acetone
[(d) Water]
Distilled water
Others
[(e) Sulfur Atom-Containing Polymerizable Monomer]
10-MDDT: 10-methacryloxydecyl-6,8-ditioctane
[(f) Acidic Group-Non-Containing Polymerizable Monomer]
UDMA: Mixture of 1,6-bis(methacrylethyloxy carbonylamino)-2,2,4-trimethylhexane and 1,6-bis(methacrylethyloxy carbonylamino)-2,4,4-trimethylhexane (Mixture of 1:1).
[(g) Curing Agent]
CQ: Camphorquinone
DMABE: 4-N,N-dimethylamino benzoic acid ethylester

Synthesis Method of 3-(Tributoxysilyl) Propyl Methacrylate

The 3-(tributoxysilyl) propyl methacrylate was synthesized by the following method. Under water prohibitive condition, 1-butanol (15.00 g) and a catalytic amount of concentrated sulfuric acid were added to 3-(trimethoxysilyl) propyl methacrylate (10.00 g) at room temperature, and the mixture was stirred at 100° C. for 16 hours. Impurities were distilled off from the reaction solution by vacuum distillation to obtain the desired 3-(tributoxysilyl) propyl methacrylate as a colorless transparent low-viscosity liquid (13.5 g) in a yield of 89%. The purity confirmed by GC was 85% or more, and the molecular structure was confirmed by $^1$H-NMR measurement and FT-IR measurement.

Synthesis Method of 3-(Tris(Pentyloxy) Silyl) Propyl Methacrylate

The 3-(tris(pentyloxy) silyl) propyl methacrylate was synthesized by the following method. Under water prohibitive condition, 1-pentanol (18.00 g) and a catalytic amount of concentrated sulfuric acid were added to 3-(trimethoxysilyl) propyl methacrylate (10.00 g) at room temperature, and the mixture was stirred at 100° C. for 18 hours. Impurities were distilled off from the reaction solution by vacuum distillation to obtain the desired 3-(tris(pentyloxy) silyl) propyl methacrylate as a colorless transparent low-viscosity liquid (14.6 g) in a yield of 87%. The purity confirmed by GC was 85% or more, and the molecular structure was confirmed by $^1$H-NMR measurement and FT-IR measurement.

Synthesis Method of 3-(Tris(Hexyloxy) Silyl) Propyl Methacrylate

The 3-(tris(hexyloxy) silyl)propyl methacrylate was synthesized by the following method. Under water prohibitive condition, 1-hexanol (20.50 g) and a catalytic amount of concentrated sulfuric acid were added to 3-(trimethoxysilyl) propyl methacrylate (10.00 g) at room temperature, and the mixture was stirred at 100° C. for 20 hours. Impurities were distilled off from the reaction solution by vacuum distillation to obtain the desired 3-(tris(hexyloxy) silyl) propyl methacrylate as a colorless transparent low-viscosity liquid (16.0 g) in a yield of 87%. The purity confirmed by GC was 85% or more, and the molecular structure was confirmed by $^1$H-NMR measurement and FT-IR measurement.

Synthesis Method of 3-(Tris(Octyloxy) Silyl) Propyl Methacrylate

The 3-(tris(octyloxy) silyl) propyl methacrylate was synthesized by the following method. Under water prohibitive condition, 1-octanol (26.50 g) and a catalytic amount of concentrated sulfuric acid were added to 3-(trimethoxysilyl) propyl methacrylate (10.00 g) at room temperature, and the mixture was stirred at 100° C. for 22 hours. Impurities were distilled off from the reaction solution by vacuum distillation to obtain the desired 3-(tris(octyloxy) silyl) propyl methacrylate as a colorless transparent low-viscosity liquid (18.8 g) in a yield of 86%. The purity confirmed by GC was 85% or more, and the molecular structure was confirmed by $^1$H-NMR measurement and FT-IR measurement.

Synthesis Method of 3-(Tris(Decyloxy) Silyl) Propyl Methacrylate

The 3-(tris(decyloxy) silyl) propyl methacrylate was synthesized by the following method. Under water prohibitive condition, 1-decanol (32.00 g) and a catalytic amount of concentrated sulfuric acid were added to 3-(trimethoxysilyl) propyl methacrylate (10.00 g) at room temperature, and the mixture was stirred at 100° C. for 24 hours. Impurities were distilled off from the reaction solution by vacuum distillation to obtain the desired 3-(tris(decyloxy) silyl) propyl methacrylate as a colorless transparent low-viscosity liquid (20.2 g) in a yield of 83%. The purity confirmed by GC was 85% or more, and the molecular structure was confirmed by $^1$H-NMR measurement and FT-IR measurement.

The adhesive strength of one liquid type dental adhesive composition prepared according to the compositions of Examples 1 to 9, 14, 17, 18 and Comparative Example 1 to 7, 9 for immediately after preparation and after storage of 50° C. was measured by the following method.

[Adhesive Strength to Porcelain (Glass Ceramics)]

An adherend (diameter: 15 mm, thickness: 5 mm) was fired using porcelain (Vintage Hallow (SHOFU INC.), and the surface of the adherend was polished with water-resistant abrasive paper #600. Then, the adherend surface of the porcelain adherend was sandblasted (0.2 MPa, 1 second) with alumina (50 μm), then was washed with water and dried, an appropriate amount of the one liquid type dental adhesive composition of Example or Comparative Example was applied to the surface and it was left to stand for 10 seconds and then air dried. After that, a stainless rod (adhesion area: (D 4.5 mm, sandblasted) applied with a paste-kneaded product of the dental adhesive resin cement (Resicem, SHOFU INC.) was pressure contacted to the adherend surface of the porcelain treated with the one liquid type dental adhesive composition of Example or Comparative Example. After removing the excess cement with a microbrush, the light was irradiated for 10 seconds by the dental polymerization LED light irradiator (PEN Bright, HOFU INC.). After immersing the prepared adhesive test specimen in water at 37° C. for 24 hours, the tensile adhesive strength with the porcelain was measured at a crosshead speed of 1 mm/min using an Instron universal testing machine (manufactured by Instron).

[Adhesive Strength to Zirconia (Oxide Ceramics)]

An adherend surface of test specimen (15 mm×15 mm×2 mm) consisting of zirconia was polished with water-resistant abrasive paper #600, was sandblasted (0.2 MPa, 1 second) with alumina (50 μm), and then was washed with water and dried. An appropriate amount of the one liquid type dental adhesive composition of Example or Comparative Example was applied to the zirconia adherend surface and it was left to stand for 10 seconds and then air dried. After that, a stainless rod (adhesion area: Φ 4.5 mm, sandblasted) applied with a paste-kneaded product of the dental adhesive resin cement (Resicem, SHOFU INC.) was pressure contacted to the adherend surface of the zirconia treated with the one liquid type dental adhesive composition of Example or Comparative Example. After removing the excess cement with a microbrush, the light was irradiated for 10 seconds by the dental polymerization LED light irradiator (PEN Bright, SHOFU INC.). After immersing the prepared adhesive test specimen in water at 37° C. for 24 hours, the tensile adhesive strength with the zirconia was measured at a crosshead speed of 1 mm/min using an Instron universal testing machine (manufactured by Instron).

[Adhesive Strength to Tooth Substance]

A test specimen of an epoxy resin embedded bovine anterior tooth was polished with water-resistant abrasive paper #600 to carve out an enamel plane and a dentin plane. An appropriate amount of the one liquid type dental adhesive composition of Example or Comparative Example was applied to the surface of the tooth substance and it was left to stand for 10 seconds and then air dried. After that, a stainless rod (adhesion area: (4.0 mm, sandblasted) applied with a paste-kneaded product of the dental adhesive resin cement (Resicem, SHOFU INC.) was pressure contacted to the tooth substance surface treated with the one liquid type dental adhesive composition of Example or Comparative Example. After removing the excess cement with a microbrush, the light was irradiated for 10 seconds by the dental polymerization LED light irradiator (PEN Bright, SHOFU INC.). After immersing the prepared adhesive test specimen in water at 37° C. for 24 hours, the tensile adhesive strength with the tooth substance was measured at a crosshead speed of 1 mm/min using an Instron universal testing machine (manufactured by Instron).

The adhesive strength of one liquid type dental adhesive composition prepared according to the compositions of Examples 10 to 13, 15, 16, 19, 20 and Comparative Example 8, 10, 11 for immediately after preparation and after storage of 50° C. was measured by the following method.

[Adhesive Strength to Porcelain (Glass Ceramics)]

An adherend (diameter: 15 mm, thickness: 5 mm) was fired using porcelain (Vintage Hallow (SHOFU INC.)), and the surface of the adherend was polished with water-resistant abrasive paper #600. Then, the adherend surface of the porcelain adherend was sandblasted (0.2 MPa, 1 second) with alumina (50 μm), then was washed with water and dried. A double-sided tape with a hole having a diameter of 4 mm was affixed to the adherend surface to prescribe an adhesion surface. An appropriate amount of the one liquid type dental adhesive composition of Example or Comparative Example was applied to the surface and it was left to stand for 10 seconds and then air dried. After that, the light was irradiated for 10 seconds by the dental polymerization LED light irradiator (PEN Bright, SHOFU INC.). A plastic mold having 4 mm of the inside diameter and 2 mm of the height was fixed on the double-sided tape with a hole, and the dental filling composite resin (BEAUTIFIL II, SHOFU INC.) was injected into the inside of the mold, and the light was irradiated for 10 seconds by the dental polymerization LED light irradiator (PEN Bright, HOFU INC.). After immersing the prepared adhesive test specimen in water at 37° C. for 24 hours, the tensile adhesive strength with the porcelain was measured at a crosshead speed of 1 mm/min using an Instron universal testing machine (manufactured by Instron).

[Adhesive Strength to Zirconia (Oxide Ceramics)]

An adherend surface of test specimen (15 mm×15 mm×2 mm) consisting of zirconia was polished with water-resistant abrasive paper #600, was sandblasted (0.2 MPa, 1 second) with alumina (50 μm), and then was washed with water and dried. A double-sided tape with a hole having a diameter of 4 mm was affixed to the adherend surface to prescribe an adhesion surface. An appropriate amount of the one liquid type dental adhesive composition of Example or Comparative Example was applied to the surface and it was left to stand for 10 seconds and then air dried. After that, the light was irradiated for 10 seconds by the dental polymerization LED light irradiator (PEN Bright, SHOFU INC.). A plastic mold having 4 mm of the inside diameter and 2 mm of the height was fixed on the double-sided tape with a hole, and the dental filling composite resin (BEAUTIFIL II, SHOFU INC.) was injected into the inside of the mold, and the light was irradiated for 10 seconds by the dental polymerization LED light irradiator (PEN Bright, HOFU INC.). After immersing the prepared adhesive test piece in water at 37° C. for 24 hours, the tensile adhesive strength with the zirconia was measured at a crosshead speed of 1 mm/min using an Instron universal testing machine (manufactured by Instron).

[Adhesive Strength to Tooth Substance]

A test specimen of an epoxy resin embedded bovine anterior tooth was polished with water-resistant abrasive paper #600 to carve out an enamel plane and a dentin plane. A double-sided tape with a hole having a diameter of 4 mm was affixed to the adherend surface to prescribe an adhesion surface. An appropriate amount of the one liquid type dental adhesive composition of Example or Comparative Example was applied to the surface and it was left to stand for 10 seconds and then air dried. After that, the light was irradiated for 10 seconds by the dental polymerization LED light irradiator (PEN Bright, SHOFU INC.). A plastic mold having 4 mm of the inside diameter and 2 mm of the height was fixed on the double-sided tape with a hole, and the dental filling composite resin (BEAUTIFIL II, SHOFU INC.) was injected into the inside of the mold, and the light was irradiated for 10 seconds by the dental polymerization LED light irradiator (PEN Bright, HOFU INC.). After immersing the prepared adhesive test piece in water at 37° C. for 24 hours, the tensile adhesive strength with the tooth substance was measured at a crosshead speed of 1 mm/min using an Instron universal testing machine (manufactured by Instron).

TABLE 1

| | (a) Silane coupling agent | | | | Silane coupling agent not satisfying the general formula (1) | | | | | | (b) Acidic group-containing polymerizable monomer | | |
|---|---|---|---|---|---|---|---|---|---|---|---|---|---|
| | SC 1 | SC 2 | SC 3 | SC 4 | SC 5 | SC 6 | SC 7 | SC 8 | SC 9 | SC 10 | 6-MHPA | 4-MET | 10-MDP |
| Example 1 | 5 | | | | | | | | | | 5 | 5 | |
| Example 2 | | 5 | | | | | | | | | 5 | 5 | |
| Example 3 | | | 5 | | | | | | | | 5 | 5 | |
| Example 4 | | | | 5 | | | | | | | 5 | 5 | |
| Example 5 | 0.01 | | | | | | | | | | 0.1 | | |
| Example 6 | 0.5 | | | | | | | | | | | | 0.5 |
| Example 7 | 0.1 | | | | | | | | | | | 3 | 2 |
| Example 8 | 1 | | | | | | | | | | | 10 | 10 |
| Example 9 | 10 | | | | | | | | | | 10 | 20 | |
| Example 10 | 1 | | | | | | | | | | | 5 | 5 |
| Example 11 | | 5 | | | | | | | | | 12 | 3 | |
| Example 12 | | | 5 | | | | | | | | 25 | 25 | |
| Example 13 | 1 | | | | | | | | | | | 5 | 5 |
| Example 14 | 15 | | | | | | | | | | 10 | 15 | |
| Example 15 | | | 5 | | | | | | | | 25 | 25 | |
| Example 16 | | 5 | | | | | | | | | 12 | 3 | |
| Example 17 | 0.01 | | | | | | | | | | 0.1 | | |
| Example 18 | 0.01 | | | | | | | | | | 1.1 | | |
| Example 19 | 1 | | | | | | | | | | | 5 | 5 |
| Example 20 | 1 | | | | | | | | | | | 5 | 5 |
| Comparative Example 1 | | 5 | | | | | | | | | | 10 | 5 |
| Comparative Example 2 | | | | | 5 | | | | | | 5 | 10 | |
| Comparative Example 3 | | | | | | 5 | | | | | 5 | 5 | |
| Comparative Example 4 | | | | | | | 5 | | | | 5 | 5 | |
| Comparative Example 5 | | | | | | | | 5 | | | 5 | 5 | |
| Comparative Example 6 | | | | | | | | | 5 | | 5 | 5 | |
| Comparative Example 7 | | | | | | | | | | 5 | 5 | 5 | |
| Comparative Example 8 | | | | | 3 | | | | | | | 10 | 10 |
| Comparative Example 9 | 1 | | | | | | | | | | | | |
| Comparative Example 10 | | 5 | | | | | | | | | 12 | 3 | |
| Comparative Example 11 | | 5 | | | | | | | | | 12 | 3 | |

| | (c) Organic solvent | (d) Water | Others | | | | |
|---|---|---|---|---|---|---|---|
| | Acetone | Distilled water | 10-MDDT | UDMA | CQ | DMABE | Aerosil OX50 |
| Example 1 | 60 | 25 | | | | | |
| Example 2 | 60 | 25 | | | | | |
| Example 3 | 60 | 25 | | | | | |
| Example 4 | 60 | 25 | | | | | |
| Example 5 | 89.89 | 10 | | | | | |
| Example 6 | 50 | 49 | | | | | |
| Example 7 | 59.9 | 35 | | | | | |
| Example 8 | 54 | 25 | | | | | |
| Example 9 | 50 | 10 | | | | | |
| Example 10 | 30 | 30 | | 28 | 0.5 | 0.5 | |
| Example 11 | 10 | 10 | 0.1 | 49.9 | 5 | 5 | |
| Example 12 | 20 | 10 | 9.8 | 5 | 0.1 | 0.1 | |
| Example 13 | 30 | 30 | | 20 | 0.5 | 0.5 | 8 |

TABLE 1-continued

|  | C1 | C2 | C3 | C4 | C5 | C6 | C7 |
|---|---|---|---|---|---|---|---|
| Example 14 | 50 | 10 |  |  |  |  |  |
| Example 15 | 10 | 10 | 9.8 | 5 | 0.1 | 0.1 |  |
| Example 16 | 5 | 15 | 0.1 | 49.9 | 5 | 5 |  |
| Example 17 | 94.89 | 5 |  |  |  |  |  |
| Example 18 | 89.89 | 9 |  |  |  |  |  |
| Example 19 | 19 | 19 |  | 20 | 0.5 | 0.5 | 30 |
| Example 20 | 37.9 | 30 |  | 20 | 0.5 | 0.5 | 0.1 |
| Comparative Example 1 | 80 | 0 |  |  |  |  |  |
| Comparative Example 2 | 55 | 25 |  |  |  |  |  |
| Comparative Example 3 | 60 | 25 |  |  |  |  |  |
| Comparative Example 4 | 60 | 25 |  |  |  |  |  |
| Comparative Example 5 | 60 | 25 |  |  |  |  |  |
| Comparative Example 6 | 60 | 25 |  |  |  |  |  |
| Comparative Example 7 | 60 | 25 |  |  |  |  |  |
| Comparative Example 8 | 40 | 30 | 1 | 5 | 0.5 | 0.5 |  |
| Comparative Example 9 | 50 | 49 |  |  |  |  |  |
| Comparative Example 10 | 0 | 20 | 0.1 | 49.9 | 5 | 5 |  |
| Comparative Example 11 | 20 | 0 | 0.1 | 49.9 | 5 | 5 |  |

TABLE 2

|  | Adhesive strength immediately after preparation [MPa] | | | | Adhesive strength after storage at 37° C. for 24 hours [MPa] | | | |
|---|---|---|---|---|---|---|---|---|
|  | Porcelain | Zirconia | Enamel | Dentin | Porcelain | Zirconia | Enamel | Dentin |
| Example 1 | 15.7 | 17.3 | 18.4 | 18.8 | 14.9 | 15.5 | 17.3 | 16.8 |
| Example 2 | 15.9 | 18.1 | 19.2 | 17.7 | 14.4 | 16.9 | 17.6 | 17.0 |
| Example 3 | 14.9 | 16.8 | 17.8 | 18.0 | 14.1 | 16.6 | 14.9 | 15.1 |
| Example 4 | 14.3 | 16.1 | 16.9 | 17.5 | 14.0 | 16.0 | 13.2 | 14.5 |
| Example 5 | 12.9 | 12.4 | 11.9 | 13.1 | 12.4 | 13.3 | 11.9 | 12.2 |
| Example 6 | 17.9 | 13.6 | 12.5 | 15.6 | 15.9 | 13.0 | 12.8 | 11.8 |
| Example 7 | 18.5 | 19.8 | 18.9 | 17.7 | 18.5 | 19.8 | 17.7 | 18.5 |
| Example 8 | 20.0 | 20.4 | 19.8 | 18.4 | 19.5 | 19.9 | 18.6 | 18.7 |
| Example 9 | 13.1 | 14.5 | 13.8 | 15.1 | 12.9 | 13.2 | 13.2 | 13.1 |
| Example 10 | 18.9 | 23.4 | 23.1 | 21.5 | 19.5 | 22.9 | 21.8 | 20.3 |
| Example 11 | 16.8 | 17.9 | 16.4 | 15.4 | 15.9 | 18.0 | 15.4 | 15.2 |
| Example 12 | 17.8 | 19.5 | 20.7 | 17.9 | 18.7 | 18.7 | 19.2 | 18.5 |
| Example 13 | 20.1 | 25.3 | 24.1 | 22.7 | 19.8 | 24.9 | 22.5 | 21.0 |
| Example 14 | 11.2 | 14.4 | 14.0 | 14.0 | 10.1 | 13.2 | 13.0 | 13.0 |
| Example 15 | 16.9 | 11.3 | 13.5 | 13.3 | 16.9 | 10.9 | 12.7 | 12.6 |
| Example 16 | 14.3 | 16.5 | 14.9 | 13.9 | 15.1 | 17.5 | 13.8 | 14.1 |
| Example 17 | 11.1 | 12.3 | 10.5 | 10.3 | 11.0 | 13.2 | 10.0 | 10.1 |
| Example 18 | 13.0 | 12.3 | 11.9 | 13.2 | 12.2 | 13.2 | 11.8 | 12.3 |
| Example 19 | 19.5 | 25.5 | 23.9 | 22.0 | 19.6 | 25.0 | 22.1 | 20.7 |
| Example 20 | 19.3 | 24.9 | 24.0 | 23.0 | 19.7 | 23.9 | 22.4 | 20.8 |
| Comparative Example 1 | 18.9 | 16.3 | 1.9 | 2.1 | 17.4 | 16.0 | 0.1 | 0.7 |
| Comparative Example 2 | 19.7 | 19.3 | 16.5 | 16.6 | 1.1 | 16.7 | 14.2 | 13.9 |
| Comparative Example 3 | 19.1 | 17.7 | 17.8 | 15.9 | 1.3 | 14.5 | 10.7 | 11.6 |
| Comparative Example 4 | 5.4 | 7.6 | 6.8 | 4.9 | 5.2 | 6.1 | 5.3 | 3.9 |
| Comparative Example 5 | 5.9 | 15.4 | 18.9 | 17.5 | 5.1 | 17.6 | 16.3 | 16.7 |
| Comparative Example 6 | 15.4 | 15.7 | 16.6 | 17.0 | 2.4 | 15.7 | 14.0 | 12.2 |
| Comparative Example 7 | 3.4 | 14.9 | 15.5 | 14.9 | 0.8 | 12.1 | 13.8 | 12.7 |
| Comparative Example 8 | 18.6 | 22.1 | 21.3 | 22.4 | 1.1 | 15.3 | 18.5 | 17.4 |
| Comparative Example 9 | 4.9 | 1.3 | 0.0 | 0.0 | 5.0 | 1.0 | 0.0 | 0.0 |

TABLE 2-continued

| | Adhesive strength immediately after preparation [MPa] | | | | Adhesive strength after storage at 37° C. for 24 hours [MPa] | | | |
|---|---|---|---|---|---|---|---|---|
| | Porcelain | Zirconia | Enamel | Dentin | Porcelain | Zirconia | Enamel | Dentin |
| Comparative Example 10 | Non-uniform (phase separation) | | | | | | | |
| Comparative Example 11 | 5.4 | 6.5 | 0.9 | 0.7 | 4.9 | 6.1 | 0.3 | 0.4 |

The one liquid type dental adhesive compositions of Examples 1-9, 14, 17 and 18 exhibited excellent adhesive property to porcelain, zirconia, enamel and dentin in both immediately after preparation and after storage at 50° C. for 4 weeks. On the other hand, adhesive property to dentin in the one liquid type dental adhesive compositions of Comparative Example 1 was low. In addition, in the one liquid type dental adhesive compositions of Comparative Examples 2, 3 and 6, adhesive property to porcelain after storage at 50° C. for 4 weeks was significantly reduced. It is considered in the one liquid type dental adhesive compositions of Comparative Examples 2, 3 and 6, because the hydrolyzable group of the compounded silane coupling agent was easily hydrolyzed, hydrolysis of the hydrolyzable group in the silane coupling agent progressed during storage, and then the generated silanol groups were condensed with each other, therefore the adhesive property to the porcelain was significantly reduced. In addition, the one liquid type dental adhesive compositions of Comparative Examples 4, 5, and 7 did not exhibit good adhesive property to porcelain immediately after preparation. It is considered in the one liquid type dental adhesive compositions of Comparative Examples 4, 5, and 7, because the hydrolyzable group of the compounded silane coupling agent was an organic group having a large sterical hinder, the hydrolysis resistance was extremely high and the silanol group was hardly generated, therefore the adhesive property with the porcelain could not be obtained immediately after the preparation. Since the one liquid type dental adhesive composition of Comparative Example 9 did not contain an acidic group-containing polymerizable monomer, sufficient adhesive property could not be obtained.

The one liquid type dental adhesive compositions of Examples 10-13, 15, 16, 19, 20 exhibited excellent adhesive property to porcelain, zirconia, enamel, and dentin in both immediately after preparation and after storage at 50° C. for 4 weeks. On the other hand, in the one liquid type dental adhesive composition of Comparative Example 8, adhesive property to porcelain after storage at 50° C. for 4 weeks was significantly reduced. Since the one liquid type dental adhesive composition of Comparative Example 10 did not contain an organic solvent, phase separation occurred, therefore a confirmation test of adhesive strength could not be performed. Since the one liquid type dental adhesive composition of Comparative Example 11 did not contain water, sufficient adhesiveness could not be obtained.

With respect to the use of substantially any plural and/or singular terms herein, those having skill in the art can translate from the plural to the singular and/or from the singular to the plural as is appropriate to the context. Although the description herein has been given with reference to the drawings and embodiments, it should be noted that those skilled in the art may make various changes and modifications on the basis of this disclosure without difficulty.

INDUSTRIAL APPLICABILITY

The present disclosure can be industrially used as one liquid type dental primer, one liquid type dental adhesive and the like in the dental field.

What is claimed is:

1. A one liquid type dental adhesive composition, comprising;
    0.01 to 10 parts by weight of a (a) silane coupling agent represented by formula (1), 0.1 to 50 parts by weight of a (b) acidic group-containing polymerizable monomer, 10 to 90 parts by weight of a (c) volatile organic solvent, and 9 to 50 parts by weight of (d) water, with respect to 100 parts by weight of a total amount of the one liquid type dental adhesive composition:

wherein, $R^1$ represents an organic group having at least one functional group selected from the group consisting of a (meth)acryloyl group, a vinyl group and an epoxy group, $R^2$ represents C4-C8 linear alkyl group, $R^3$ represents C1-C8 alkyl group, and n is integer selected from 1 to 3.

2. The one liquid type dental adhesive composition of claim 1, wherein
    the (a) silane coupling agent is represented by formula (2):

wherein, $R^1$ represents an organic group having at least one (meth)acryloyl group, and $R^2$ represents C4-C8 linear alkyl group.

3. The one liquid type dental adhesive composition of claim 1, wherein
    the (a) silane coupling agent is represented by formula (3):

wherein, $R^1$ represents a C3-C8 alkyl group having at least one (meth)acryloyl group, and $R^2$ represents C4-C8 linear alkyl group.

4. The one liquid type dental adhesive composition of claim 1, wherein
    the one liquid type dental adhesive composition further contains one or more members selected from the group consisting of (e) sulfur atom-containing polymerizable monomer, (f) non-acidic group containing polymerizable monomer and (g) curing agent.

5. The one liquid type dental adhesive composition of claim 2, wherein
the one liquid type dental adhesive composition further contains one or more members selected from the group consisting of (e) sulfur atom-containing polymerizable monomer, (f) non-acidic group containing polymerizable monomer and (g) curing agent.

6. The one liquid type dental adhesive composition of claim 3, wherein
the one liquid type dental adhesive composition further contains one or more members selected from the group consisting of (e) sulfur atom-containing polymerizable monomer, (f) non-acidic group containing polymerizable monomer and (g) curing agent.

7. The one liquid type dental adhesive composition of claim 1, wherein
the (b) acidic group-containing polymerizable monomer is one or more selected from the group consisting of (b-1) phosphate group-containing polymerizable monomer, (b-2) pyrophosphate group-containing polymerizable monomer, (b-3) carboxylic acid group-containing polymerizable monomer and (b-4) sulfonic acid group-containing polymerizable monomer.

8. The one liquid type dental adhesive composition of claim 1, wherein
the (b) acidic group-containing polymerizable monomer is a polymerizable monomer containing a divalent phosphate group.

9. The one liquid type dental adhesive composition of claim 1, wherein
the one liquid type dental adhesive composition comprises 5 to 20 parts by weight of the (b) acidic group-containing polymerizable monomer with respect to 100 parts by weight of the total amount of the one liquid type dental adhesive composition.

10. The one liquid type dental adhesive composition of claim 1, wherein
the (c) volatile organic solvent is a water soluble volatile organic solvent having a boiling point of 100° C. or lower under ordinary pressure.

11. The one liquid type dental adhesive composition of claim 1, wherein
the one liquid type dental adhesive composition comprises 30 to 60 parts by weight of the (c) volatile organic solvent with respect to 100 parts by weight of the total amount of the one liquid type dental adhesive composition.

12. The one liquid type dental adhesive composition of claim 1, wherein
the one liquid type dental adhesive composition comprises 25 to 35 parts by weight of the (d) water with respect to 100 parts by weight of the total amount of the one liquid type dental adhesive composition.

13. The one liquid type dental adhesive composition of claim 1, wherein
the one liquid type dental adhesive composition further comprises 0.01 to 10 parts by weight of a (e) sulfur atom-containing polymerizable monomer with respect to 100 parts by weight of the total amount of the one liquid type dental adhesive composition.

14. The one liquid type dental adhesive composition of claim 1, wherein
the one liquid type dental adhesive composition further comprises 5 to 50 parts by weight of an (f) acidic group-non-containing polymerizable monomer with respect to 100 parts by weight of the total amount of the one liquid type dental adhesive composition.

15. The one liquid type dental adhesive composition of claim 1, wherein the one liquid type dental adhesive composition further comprises 0.1 to 30 parts by weight of a (h) filler with respect to 100 parts by weight of the total amount of the one liquid type dental adhesive composition.

\* \* \* \* \*